(12) United States Patent
Martin (10) Patent No.: US 6,355,157 B1
(45) Date of Patent: Mar. 12, 2002

(54) PROCESS FOR REAL-TIME DETECTION AND INHIBITION OF LOCALIZED CORROSION

(75) Inventor: Roy Martin, Downers Grove, IL (US)

(73) Assignee: United States Filter Corporation, Palm Desert, CA (US)

(*) Notice: Subject to any disclaimer, the term of this patent is extended or adjusted under 35 U.S.C. 154(b) by 0 days.

(21) Appl. No.: 09/603,763

(22) Filed: Jun. 22, 2000

(51) Int. Cl.[7] .................... G01N 17/04; G01N 27/27
(52) U.S. Cl. .................. 205/775.5; 205/777; 204/404; 324/700
(58) Field of Search ................ 204/404; 205/775.5, 205/791, 776.5, 777

(56) References Cited

U.S. PATENT DOCUMENTS

| | | | |
|---|---|---|---|
| 4,575,678 A | | 3/1986 | Hladky ............. 204/404 |
| 5,139,627 A | * | 8/1992 | Eden et al. ......... 204/404 |
| 5,888,374 A | | 3/1999 | Pope et al. ......... 205/775.5 |
| 6,015,484 A | * | 1/2000 | Martinchek et al. ... 205/775.5 |
| 6,068,012 A | * | 5/2000 | Beardwood et al. ..... 137/3 |
| 6,132,593 A | * | 10/2000 | Tan ................. 205/776.5 |

OTHER PUBLICATIONS

Mansfeld et al "Electrochemical Noise Analysis of Iron Exposed to NaCl Solutions of Different Corrositivity", J. Electrochem. Soc. 140, pp. 2205–2209, 1993.*

Brusamarello et al. "Analysis of Different Methods to Calculate Electrochemical Noise Resistance Using a Three–Electrode Cell", Corrosion, 55, pp. 273–282, 2000.*

Eden, Comments on Mansfeld et al (J. Electrochem. Soc. 140, pp. 2205–2209, 1993), J. Electrochem. Soc. 141, pp. 1402–1404, 1994.*

* cited by examiner

*Primary Examiner*—Robert J. Warden, Sr.
*Assistant Examiner*—Kaj K. Olsen
(74) *Attorney, Agent, or Firm*—Wolf, Greenfield & Sacks, P.C.

(57) ABSTRACT

This invention describes a novel means of determining the nature (type) of corrosion in real-time. By identifying localized corrosion at the moment of pit initiation, real-time selection, and effective concentration(s) of appropriate inhibitor(s) can be delivered to an electrolytic solution before propagation of the localized corrosion. Integrating this information with a corrosion inhibitor feed system can effectively inhibit the corrosion before propagation occurs, thereby maintaining system integrity. The process embodies a method of operation wherein the electrochemical noise (ECN) and linear polarization (LPR) values are processed to compare how the corrosion signals correlate. Divergence of the corrosion rates indicates the formation of localized corrosion while continuity in signal pattern indicates generalized corrosion.

4 Claims, 10 Drawing Sheets

PROCESS FOR REAL-TIME DETECTION AND INHIBITION OF LOCALIZED CORROSION

FIELD OF THE INVENTION

This invention relates to a means for determining corrosive conditions and a process for its use. The invention particularly relates to real-time detection of the initiation of localized corrosion, thereby enabling commencement of appropriate anti-corrosion counter measures to prevent or minimize equipment damage.

BACKGROUND OF THE INVENTION

Heat transfer equipment (heat exchangers) in contact with an electrolyte is subject to corrosion. Corrosion is the primary cause of system failures resulting in high maintenance labor and lost production. To inhibit corrosion, various types of chemical inhibitors are applied along with other supporting chemical treatments in an effort to control the nature and rate of corrosion. It has long been desired to be able to optimize inhibitor concentrations based on real-time program performance. However, such attempts have met with only minimal success.

The two categories of inhibitors common to cooling water treatment applications are cathodic and anodic inhibitors. Water treatment programs may incorporate one or more corrosion inhibitors based on the method(s) of corrosion inhibition. Also, specialty polymers are commonly applied with the selected corrosion inhibitor to inhibit uncontrolled precipitation of the corrosion inhibitor. Therefore, in order to select the appropriate inhibitor(s) and optimize their concentration in the electrolytic solution, e.g. cooling water, the nature of corrosion needs to be accurately determined.

It is desirable to inhibit localized corrosion upon detection, e.g. to minimize the severity of the pitting of carbon steel and/or to minimize stress corrosion cracking on stainless steel induced, for example, by the presence of chlorides, as well as to reduce the insulating effects caused by the accumulation of corrosion byproducts. This is particularly critical in high temperature heat exchangers, where extending the period the metal is exposed to localized corrosion can induce premature failure of the heat transfer equipment.

Many systems experience periodic upsets that can dramatically increase the onset and rate of corrosion. These upsets can result from numerous process deviations, e.g. increased concentrations of corrosion inducing ions in the incoming water (such as chlorides and sulfates) or process leaks that contaminate the water. During upset conditions, localized corrosion is usually the dominant method of corrosion. If the concentration of inhibitor(s) in the cooling water is not adjusted to compensate for the upset, severe damage to the heat transfer surfaces, as well as supporting equipment results.

Prior art processes teach of storing data, e.g. electrochemical noise data (ECN), and using said data to calculate a slope of the amplitude to determine the nature of the corrosion. This methodology necessitates extensive collection of data over time. During the period of collecting these values and determining the slope generated from the data obtained from a Fourier Transform, propagation of pitting, metal dissolution, and accumulation of corrosion byproducts continues unabated, thereby compromising the equipment integrity. Since the prior art methodology requires as much as hours of inputs and interpretation thereof, localized corrosion on heat transfer equipment will continue to occur.

Corrosion inhibitors are currently controlled by various devices in an attempt to maintain a predetermined concentration. The desired inhibitor concentration is determined based on guidelines established via test data, field experience, and historical data obtained by site specific monitoring. This methodology fails to appreciate the criticality of real-time detection to minimize the deleterious effects of corrosive conditions.

Thus, in order to quickly suppress corrosion, the nature of corrosion must be identified so that appropriate selection and levels of inhibitor(s) are administered. For example, because of the severity of localized corrosion, identification of pitting corrosion at the moment of pit initiation is highly desirable. If the pitting can be quickly detected and identified during the initial stage and inhibited before propagation of the pitting, minimal loss of metal and accumulation of corrosion byproducts occurs. System integrity is managed, resulting in improved operational performance, increased reliability and equipment life.

DESCRIPTION OF THE PRIOR ART

U.S. Pat. No. 4,575,678 describes an apparatus having two metal parts corroding in an electrolyte and separated by an insulator. The low frequency voltage and current between the electrodes is observed. This low voltage and current is a low frequency noise signal. Amplitude values of the signals are measured and computed yielding data indicating the corrosion rate and the nature of corrosion. This method of corrosion measuring is commonly referred to as electrochemical noise (ECN).

U.S. Pat. No. 5,888,374 (US Government has rights pursuant to contract with Argonne National Laboratory) describes a means of monitoring localized pitting corrosion. The patent describes storing values from Electro-Chemical Noise sensors and processing the stored values utilizing Fourier Transform. A slope of the power spectral density data relative to frequency is calculated. The data is trended over time (hours) to determine the subtle deviations in the slope.

The prior art fails to recognize the need for real-time detection and evaluation of corrosion conditions and the need to integrate such data with corrosion inhibiting measures.

SUMMARY OF THE INVENTION

This invention describes a novel means of determining the nature (type) of corrosion in real-time. The real-time analysis of upset conditions has now been recognized as a valuable tool in both the detection and forecasting of localized corrosion. This is especially useful when replicating the operational and environmental conditions between metals and electrolyte in heat exchangers. By identifying localized corrosion at the moment of pit initiation, real-time selection, and effective concentration(s) of appropriate inhibitor(s) can be delivered to an electrolytic solution before propagation of the localized corrosion.

Prior art processes have historically relied on a methodology requiring the storing of electrochemical noise data, and using said data to calculate a slope to determine the nature of the corrosion. The delay in identifying the onset and type of corrosion inherent in this methodology often results in severe, and sometimes catastrophic, damage to associated equipment. Furthermore, heat transfer properties are often compromised due to the insulating effects caused by the accumulation of corrosion byproducts.

The instant method provides real-time identification of localized corrosion during the initial stage of formation.

Integrating this invention with corrosion inhibitor feed can effectively inhibit the corrosion before propagation occurs, thereby maintaining system integrity. The process embodies a method of operation wherein the electrochemical noise (ECN) and linear polarization (LPR) values are processed to compare how the corrosion signals correlate. Divergence of the corrosion signals indicates the formation of localized corrosion while continuity in signal pattern indicates generalized corrosion.

Accordingly, it is an objective of the instant invention to teach a device and a process for its use which can identify corrosion, particularly localized corrosion, in real-time during the initial stage of pit formation.

It is an additional objective of the instant invention to integrate the corrosion identifying process with a process for corrosion inhibition which can quickly suppress the corrosion cell(s) by making real-time adjustments to the inhibitor program.

It is yet an additional objective of the instant invention to teach a process for monitoring corrosion values for both electrochemical noise (ECN) and linear polarization (LP) under heat transfer.

It is still an additional objective of the instant invention to teach a method of operation wherein the ECN and LP values are processed to compare how the corrosion signals correlate.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

This invention describes a novel means of determining the nature (type) of corrosion in real-time. By identifying localized corrosion at the moment of pit initiation, real-time selection, and effective concentration(s) of appropriate inhibitor(s) can be delivered to an electrolytic solution before propagation of the localized corrosion.

The instant process can identify the localized corrosion during the initial stage of pit formation and quickly suppress the corrosion cell(s) by making real-time adjustments to the inhibitor program.

In order to produce a real-time determination of corrosive conditions, the present invention monitors corrosion values for both electrochemical noise and linear polarization under heat transfer conditions. The values are processed to compare how the corrosion signals correlate. Divergence of the processed corrosion signals indicates the formation of localized corrosion while continuity in signal pattern indicates generalized corrosion. The ability to provide real-time identification of localized corrosion during the initial stage of pit formation enables integration of this invention with corrosion inhibitor feed equipment to effectively inhibit the corrosion before propagation occurs, thereby maintaining system integrity.

Figure 1:
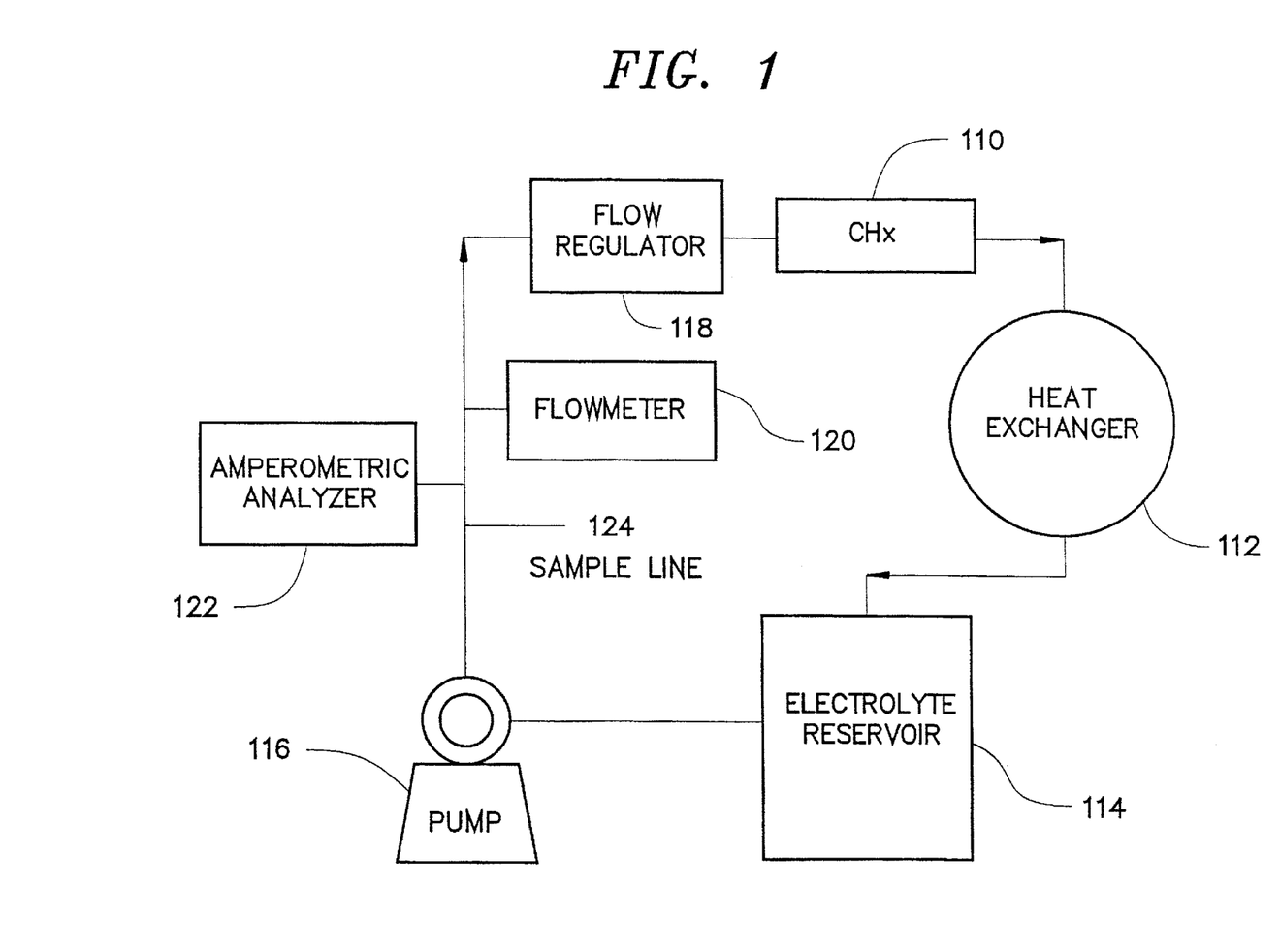
FIG. 1 is illustrative of a circulating system useful for conducting tests replicating a typical cooling water treatment application.

FIG. 1 is illustrative of a circulating system useful for conducting tests replicating a typical cooling water treatment application. Referring to FIG. 1, the instant device is comprised of a system that incorporates: a MENTOR CHx heat transfer device (see FIG. 2) 110 that is made of the metallurgy to be tested. The metallurgy under heat transfer is in contact with an electrolyte which is pumped via pump 116 through a heat exchanger 112 through which electrolyte from electrolyte reservoir 114 is passed. The electrolyte flow rate is adjusted to desired levels by adjusting flow regulator 118. A flowmeter 120 is in fluid communication for ease of adjustments. If added, the concentration of a passivator is measured using a standardized amperometric analyzer. A sample line 124 is optionally provided for convenience in withdrawing samples for testing.

Figure 2:
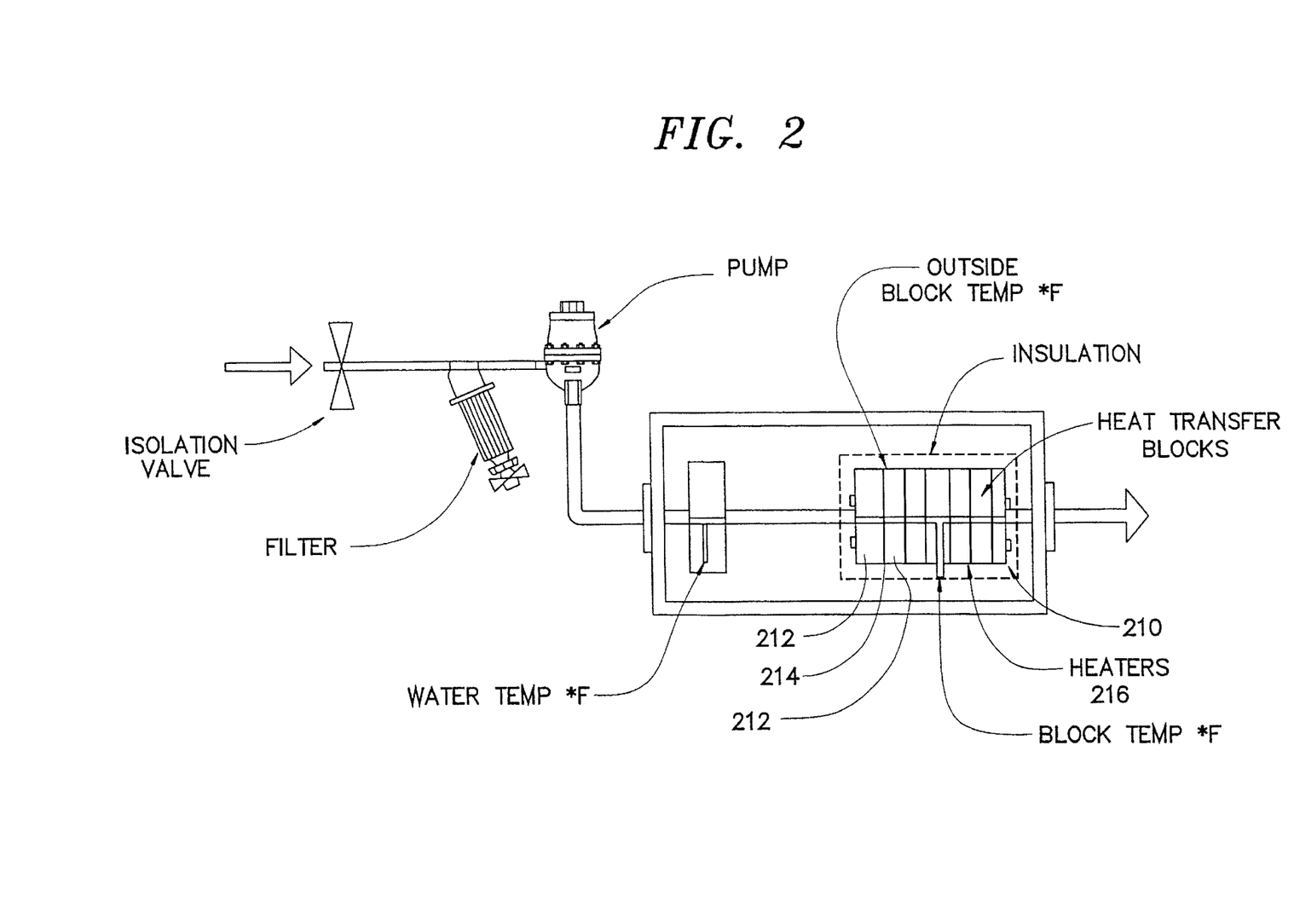
FIG. 2 illustrates a cross-sectional view of a MENTOR CHx device.

With reference to FIG. 2, a MENTOR CHx device is illustrated. For our testing we utilized the MENTOR-CHx system, available from Integriti Solutions Corp., to simulate the conditions associated with heat transfer equipment.

The metallurgies corrosion rates are measured using electrochemical noise (ECN) and Linear Polarization (LPR) probes (not shown); the measured ECN and LPR data are input to a remote computer which is constructed and arranged for mathematically correlating the ECN and LPR data; the resulting correlation is used to identify the nature of the corrosion.

The MENTOR system determines the nature of corrosion, e.g. the change in steady state conditions, by calculating a Localization Index (LI) which is equal to $\sigma_i / i_{rms}$, where $\sigma_i$ and $i_{rms}$ are the standard deviation and root mean square of the noise current respectively. Increases over time are assumed to be indicative of a localized corrosion process taking place.

In applications where passivators are applied to the electrolyte this method is susceptible to error. Passivators increase the current until the critical current density is achieved. The corresponding increase in current increases the LI indicating localized corrosion, when in fact, the metal is merely being passivated. Without additional data, a simple incident such as a grain of sand etching a metallic surface might well give the system operators a false positive, causing them to believe that localized corrosion has been occurring. This might instigate them to add inhibitors of an inappropriate type or at an inappropriate concentration, when merely waiting for a period of time would allow the ambient passivator concentration to self-correct the irregularity. Furthermore, an extensive data gathering period, followed by development of the collected data, will permit significant equipment damage to occur.

The instant invention compares values consistent with measuring electrochemical noise and linear polarization corrosion techniques wherein a clear distinction can be made of the nature of corrosion even in the presence of said passivators.

The data clearly demonstrates that the instant process can use the LI calculation to indicate current activity (later referred to as the activity factor (AF)). When current activity is identified by a rise in the AF, data consistent with the measurement of LPR corrosion rate is compared thereto.

When the AF & LPR corrosion rate follow a uniform pattern, the corrosion is generalized corrosion. However, when the slopes of said values diverge, the instant inventors have identified this as a primary indication of the onset of pitting or localized corrosion.

This method of determining the nature of corrosion is superior to prior art techniques, particularly in systems where the electrolyte is treated with oxidizers &/or passivating agents, for example peroxygen compound selected from hydrogen peroxide, sodium peroxide, sodium perborate, peroxycarboxylic acids, potassium monopersulfate, sodium peroxydisulfate, potassium peroxide, potassium perborate, sodium monopersulfate, potassium peroxydisulfate, ammonium peroxydisulfate, ammonium monopersulfate and mixtures thereof, nitrites, nitrates, chromates, and the like. Recognition of the onset of localized corrosion permits immediate action to be taken to neutralize corrosive conditions before damage occurs. The appropriate type and amount of inhibitor can be immediately dosed to the system, eliminating any damage from pitting.

Now with further reference to FIG. 2, a block 210 is comprised of a series of pieces of the desired metallurgy 212 that are joined with an insulating material 214 placed between each adjoining piece. This series of adjoined pieces will be designated the "block". A hole (not shown) is incorporated at some part of the construction process through which the electrolyte will contact the block. The metal pieces making up the block are equipped with appropriate sensing apparatus (not shown) for the sensing of ECN and LPR. Other sensing apparatus for determination of temperature gradients, heat transfer coefficients, etc. can be applied in a way that does not interfere with the performance of ECN and LPR sensing apparatus. The block is equipped with a device 216 to provide heat thru the block. The block is combined with other supporting equipment necessary for replicating the operational environment of the heat transfer equipment in question. This can include, but is not limited to, equipment necessary for replicating electrolyte flow rate, electrolyte chemical parameters, and skin temperature at the heat exchanger electrolyte interface, etc.

The process control parameters are adjusted and controlled to replicate the operational environment at the heat exchanger metal-electrolyte interface.

Both ECN and LPR corrosion data are monitored and the data is inputted to a computer (not shown) that utilizes methods for correlating their trend on a real-time basis. Continuity in the trend illustrates generalized or uniform corrosion. Divergence in the trend identifies the onset of localized corrosion.

Test Results

All testing was performed at a skin temperature of 144° F. using 1010 carbon steel. Flowrate was regulated at 3.8 gpm.

Corrosion values consistent with electrochemical noise corrosion and linear polarization corrosion measuring techniques are correlated to determine the nature of corrosion. The "Activity Factor" (AF) is calculated using the equation:

$$AF = \sigma_i / i_{rms}$$

where $\sigma_i$ is the standard deviation of the electrochemical current noise data, and $i_{rms}$ is the root mean square of the electrochemical current noise.

The AF detects changes in current and highlights the deviation from the steady state condition. However, it alone does not indicate the nature of corrosion since increased oxidation potential of the electrolyte such as with the addition of passivating agents will increase current, and induce an increase in AF.

Because the data collected using electrochemical noise (ECN) corrosion techniques is non-intrusive, the corrosion data is clean of interferences like the applied potential technique linear polarization. For this reason, the data is related to those mechanisms directly involved with electrochemical processes (corrosion). When ECN electrodes are exposed to either a pitting or passivating environment, the electrochemical noise current increases, thereby indicating an increase in AF, and typically a corresponding increase in ECN corrosion rate.

LPR is an intrusive technique that applies a current that polarizes the electrode. Because LPR is an intrusive technique for measuring corrosion, the technique is limited to measuring changes in the overall corrosion rate. When the LPR electrode is polarized, then depolarized as a result of exposure to a pitting environment, the initial measured corrosion rate decreases. However, when LPR electrodes are depolarized, then exposed to a passive environment, the initial measured corrosion rate increases. This phenomena is a result of the difference in driving force that induces the flow of current. In the first case, the driving force is the formation of a large cathode around the small anode (pit). In the later case, the driving force is the high potential passivating agent in the electrolyte.

When a large cathode forms, the large cathodic area is highly polarized and exhibits an increased resistance. Because LPR corrosion rates are directly related to resistance by the equation:

$$MPY = K/Rp \quad (A)$$

where:
K is the Stern-Geary constant (generally available from the literature and dependent upon the metal/environment combination)
A is the electrode surface area
Rp is the polarization resistance
where $Rp = \Delta E/\Delta I$ (change in potential/change in current).

It has been discovered that the characteristics of LPR can be used in combination with the true readings of ECN to determine the nature of corrosion. Once the true nature of corrosion is determined, appropriate selection and addition of corrosion inhibitors can be applied in real-time to prevent the propagation of localized corrosion.

Although the examples herein compare LPR corrosion rate to AF, the instant invention contemplates similar comparisons which could be made, e.g. by comparing electrochemical noise corrosion rate versus LPR corrosion rate or comparing LPR resistance versus AF or ECN corrosion rate.

Test 1:
A passivating agent was added to the electrolyte to induce passivation of the electrodes. The electrolyte was circulated through the CHx (MENTOR CHx) until steady state was reached.

The concentration of passivator was measured using both a standardized amperometric sensor, and wet chemistry methodology. The concentration needed to sustain the passive condition was maintained throughout the testing period.

Figure 3:
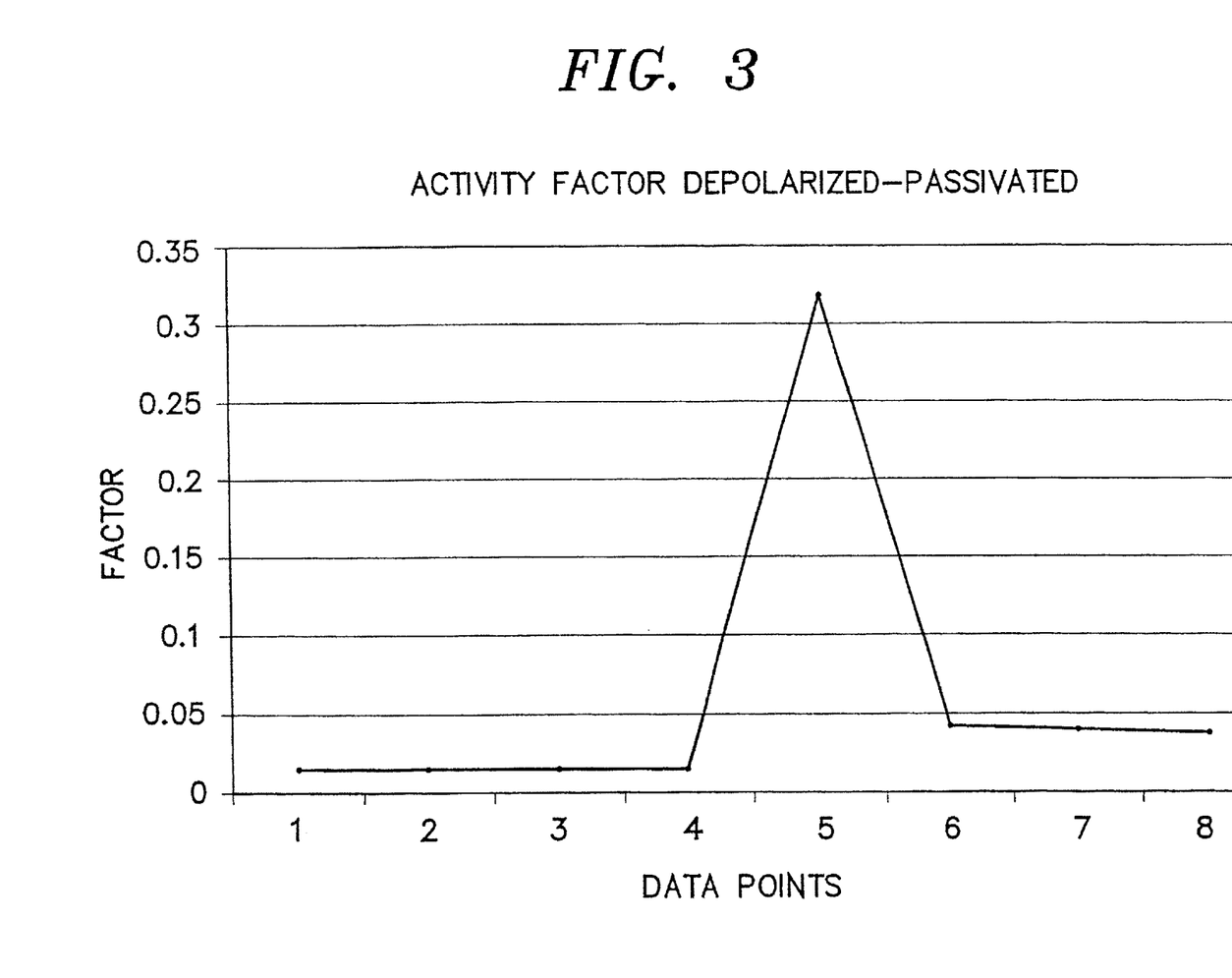
FIG. 3 is a graphical representation of Activity Factor for a Depolarized-Passivated Sample.
Figure 4:
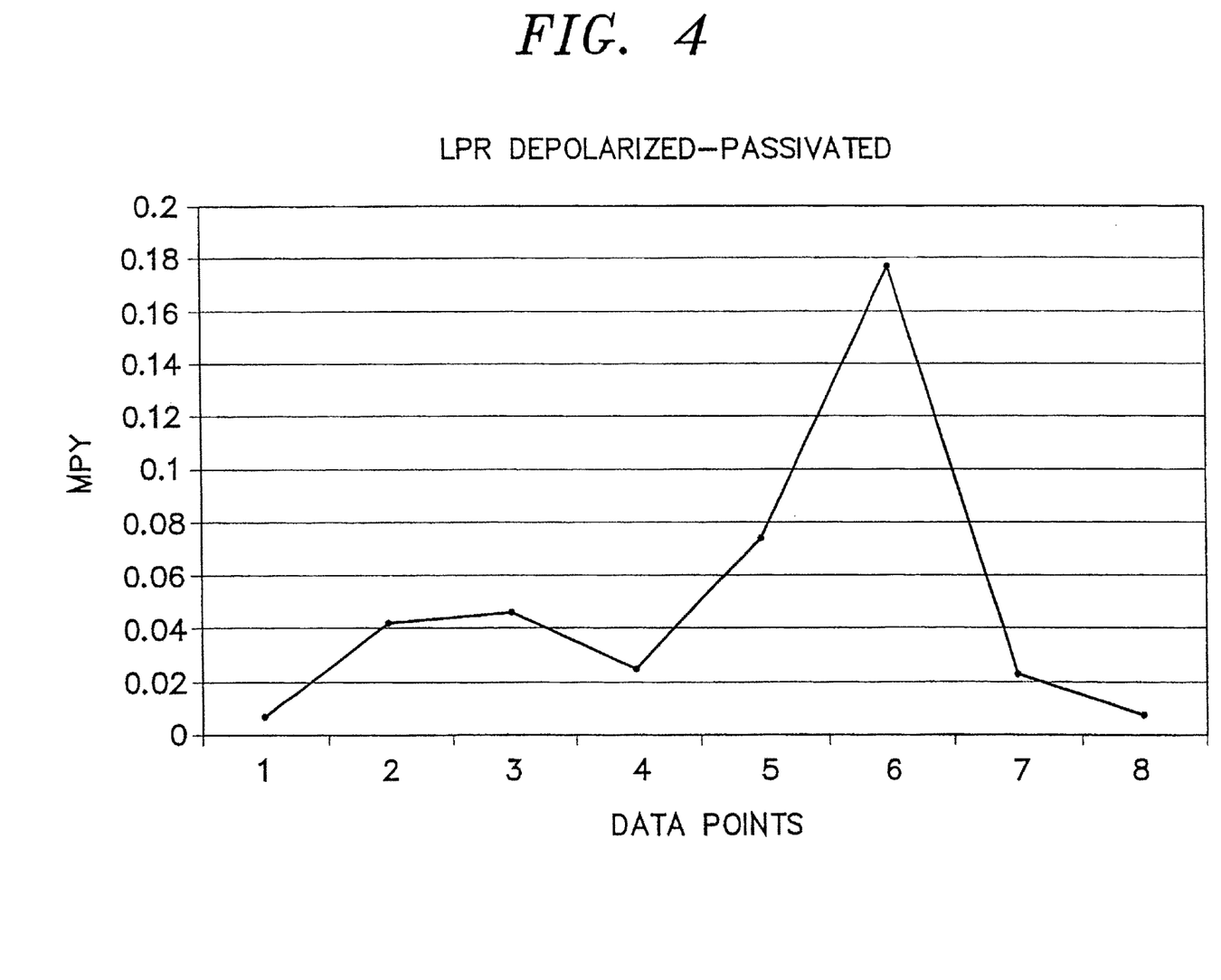
FIG. 4 is a graphical representation of Linear Polarization Rate for a Depolarized-Passivated Sample.
Figure 5:
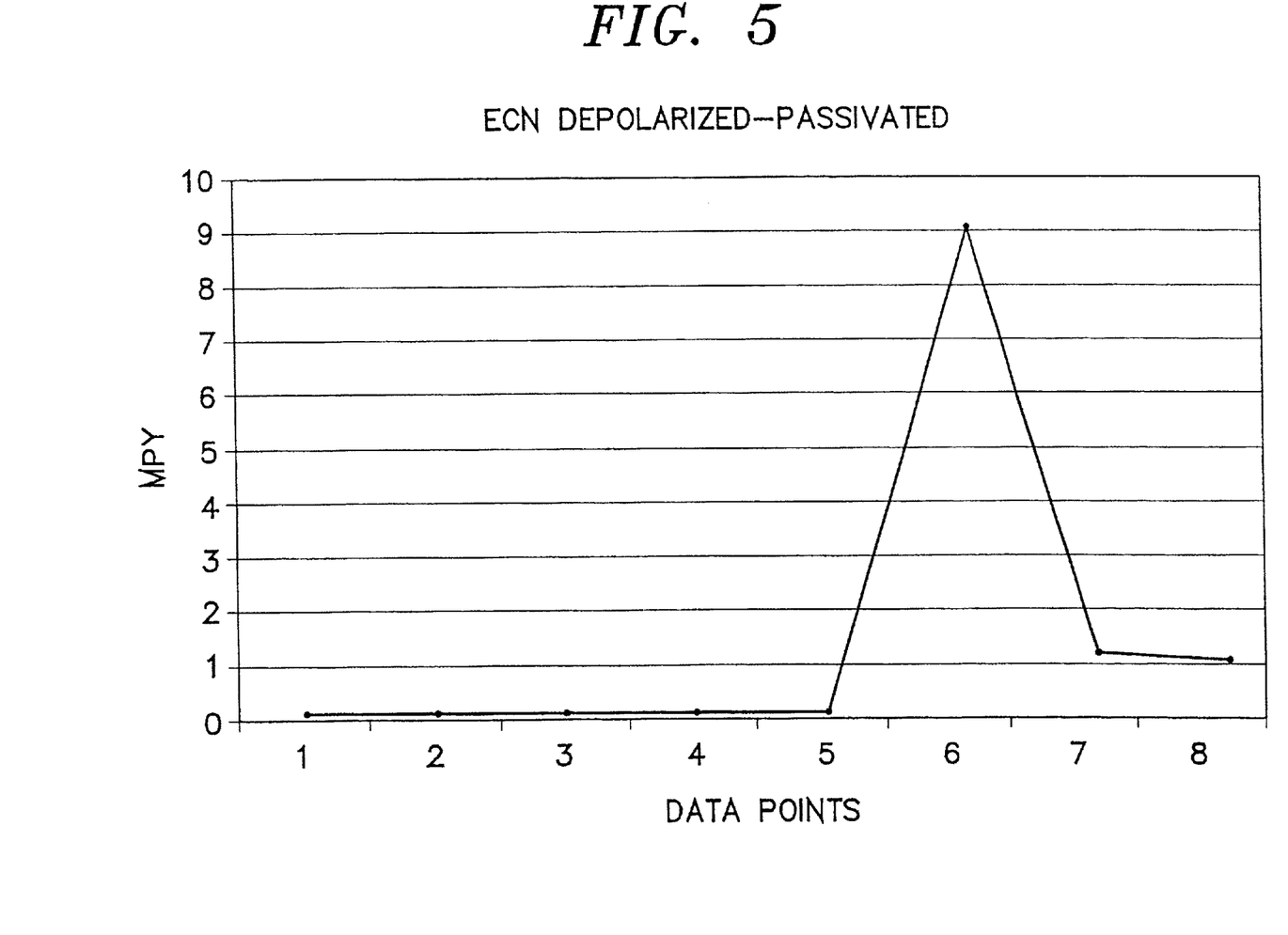
FIG. 5 is a graphical representation of Electrochemical Noise for a Depolarized-Passivated Sample.

Referring to FIGS. 3 and 4, the LPR and AF illustrate the passivated and steady state condition (data points 1–4). FIG. 5 illustrates corresponding true ECN corrosion rates in terms of mils per year (MPY).

Between data points 4 & 5, the electrodes were depolarized as indicated by the AF and measured corrosion rate. When the AF is compared to the LPR, a magnitude(s) increase in both values is observed. By data point 6, the electrodes are re-polarized by the high oxidation potential of the electrolyte. The rapid flux of electrons during the passivation process occurred over the entire exposed (depolarized) surface relating to an increased corrosion rate.

Figure 6:
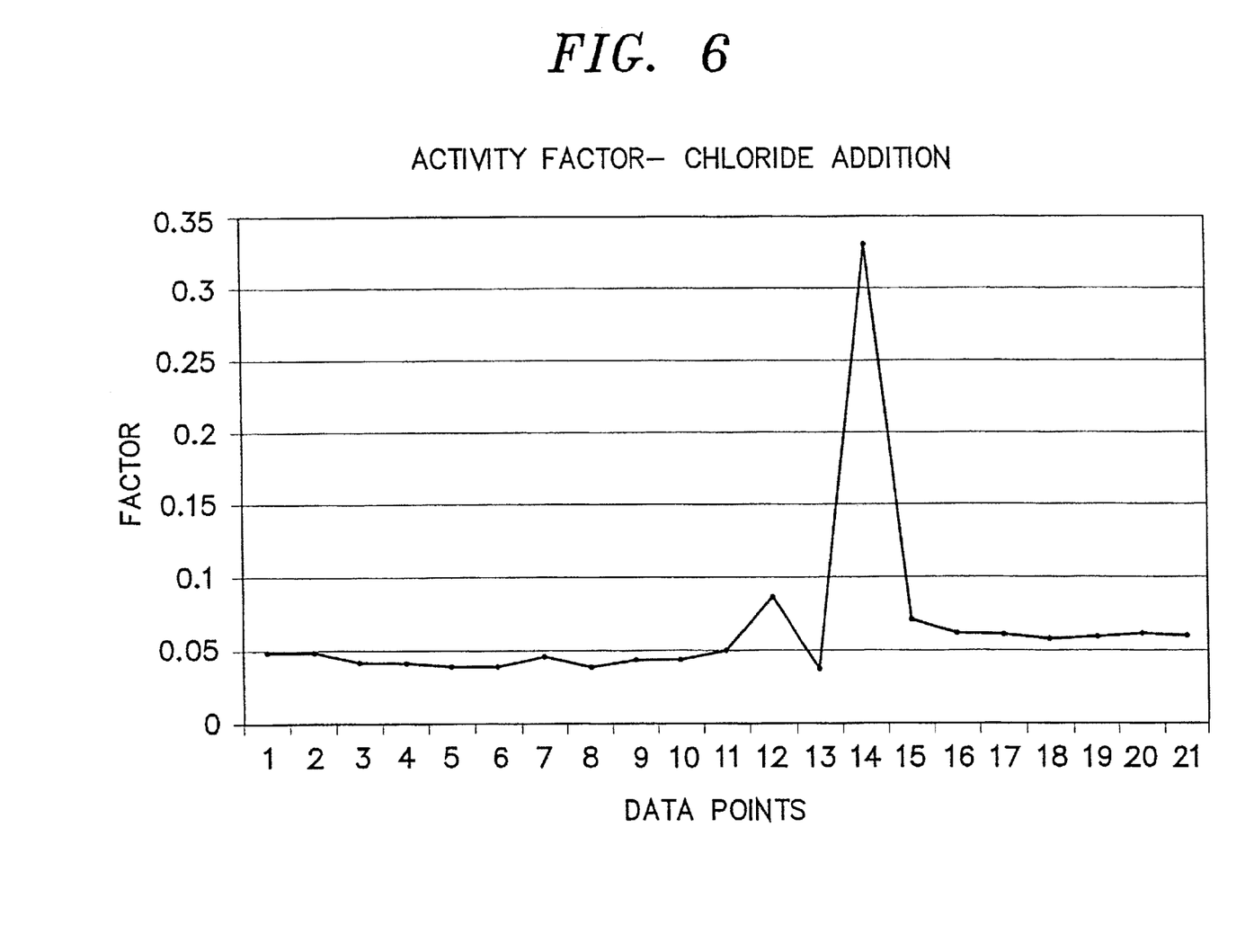
FIG. 6 is a graphical representation of Activity Factor for a Sample with Chloride Addition.
Figure 7:
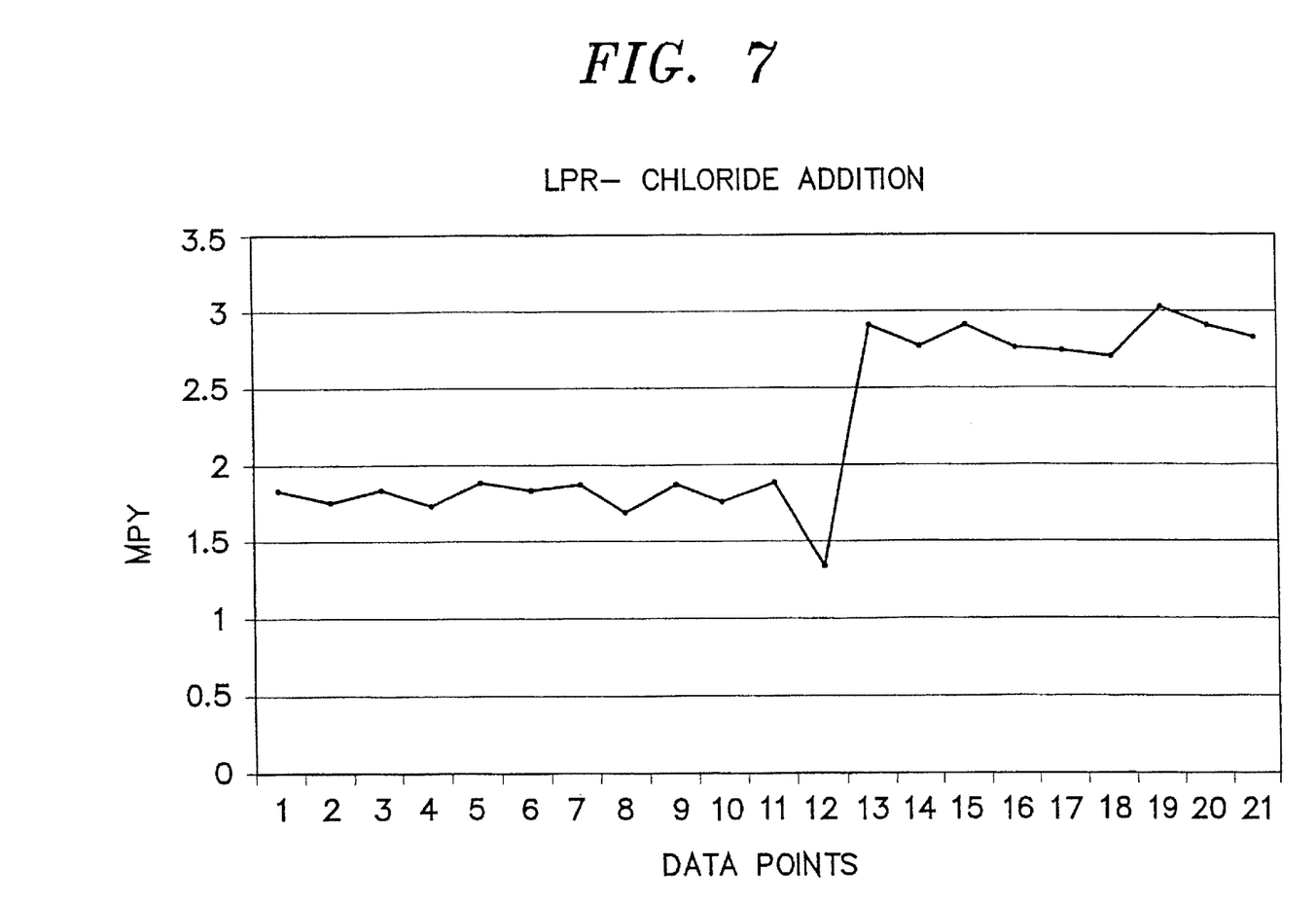
FIG. 7 is a graphical representation of Linear Polarization Rate for a Sample with Chloride Addition.

Test 2:

In this test, the same operating conditions were achieved. Referring to FIGS. 6 and 7 data points from 1–11 illustrate a steady state condition. 100 ppm of chlorides as Cl was added to the electrolyte.

Comparing data point 12 for AF & LPR, we see a divergence in signal. LPR corrosion rate significantly decreases while AF significantly increases (we can also see an increase in true ECN corrosion rate, FIG. 8).

Figure 8:
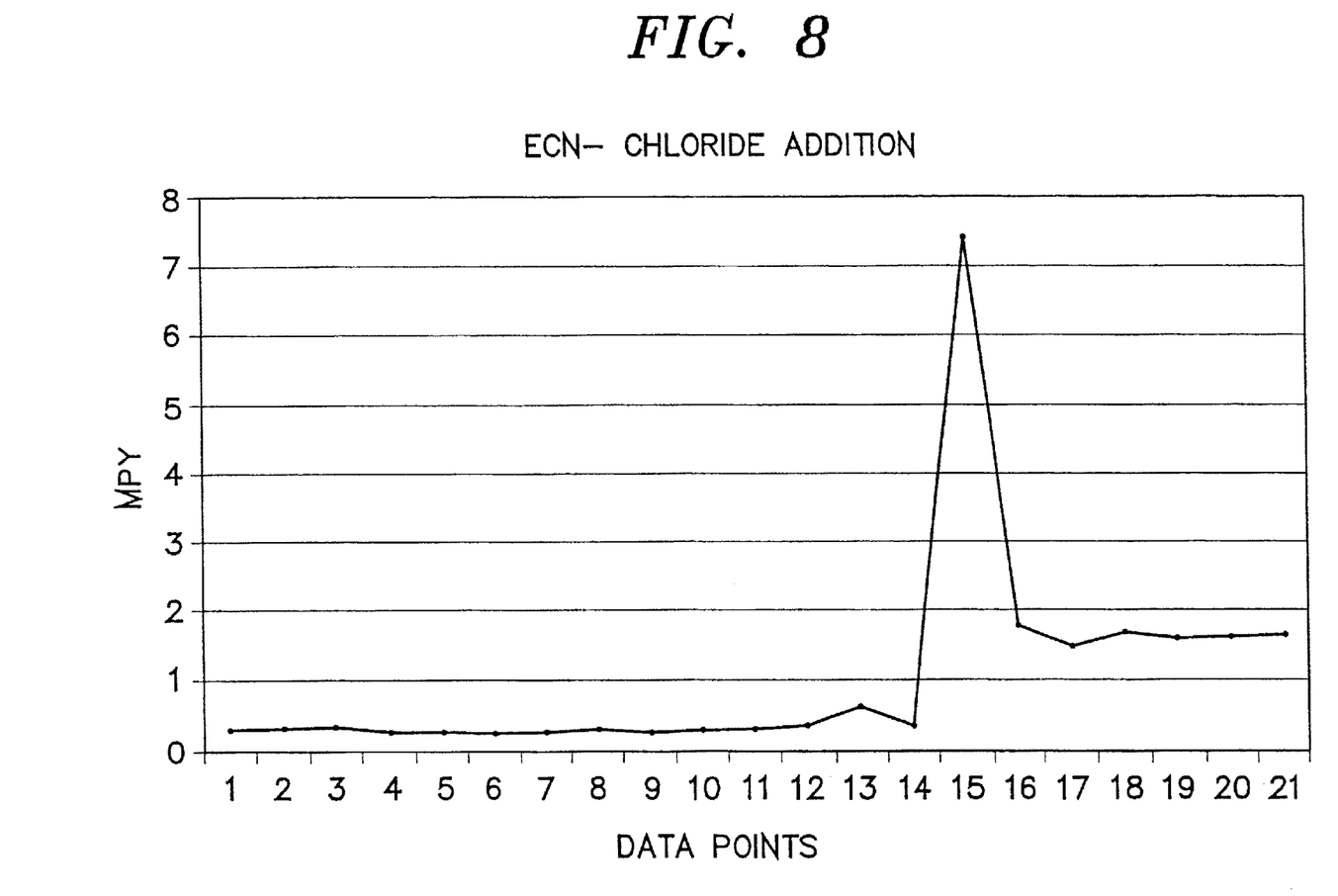
FIG. 8 is a graphical representation of Electrochemical Noise for a Sample with Chloride Addition.

The chlorides initiate localized corrosion. The change in current (compared to the steady state condition) is immediately detected by the AF. Because the current flow was localized (limited), the LPR corrosion rate is calculated to be low. The LPR indicates the corrosion rate has significantly decreased.

After detection, 50 ppm of passivating agent was added to the electrolyte and the electrodes are re-polarized by data point 15.

Figure 9:
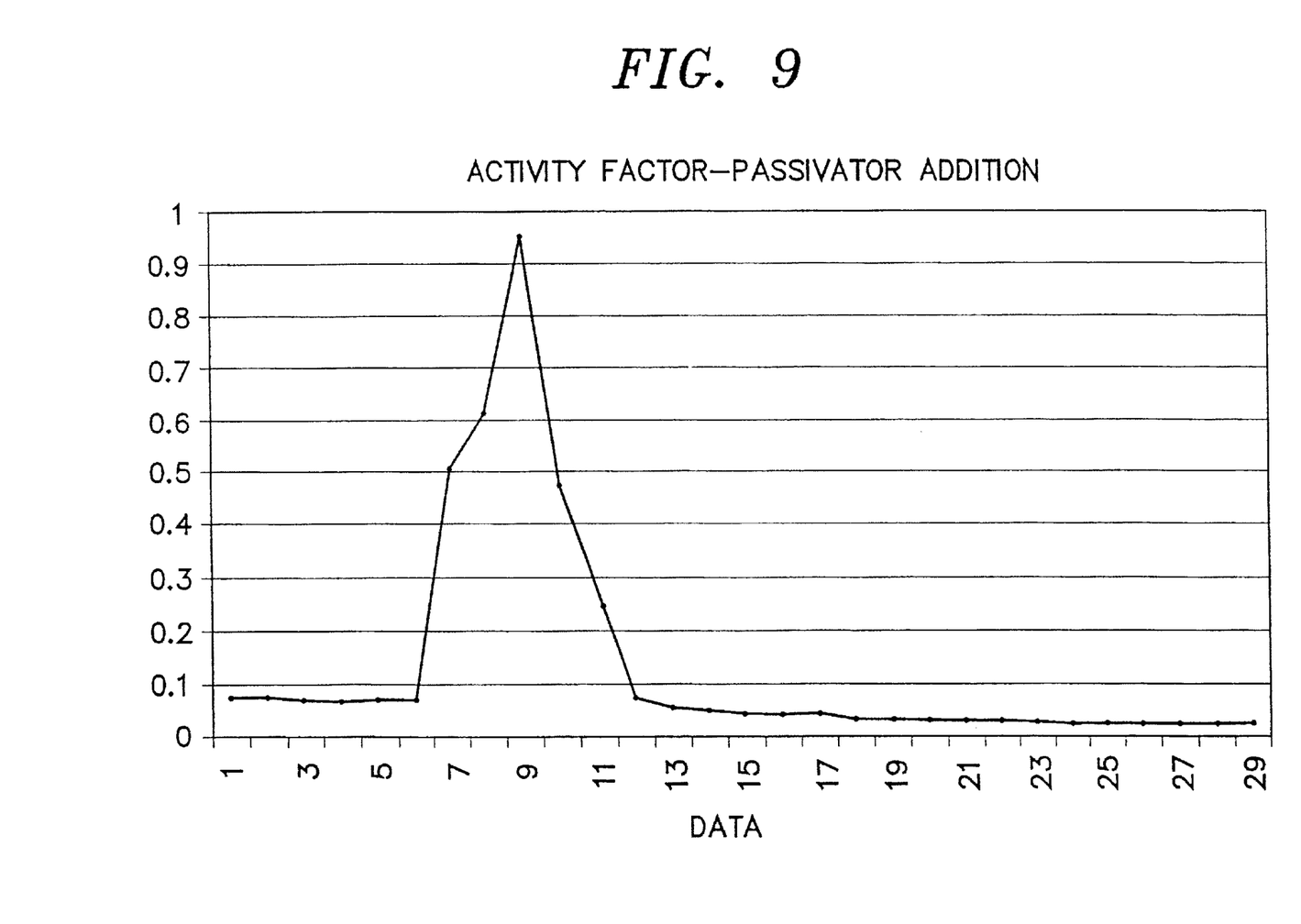
FIG. 9 is a graphical representation of Activity Factor for a sample with passivator addition.
Figure 10:
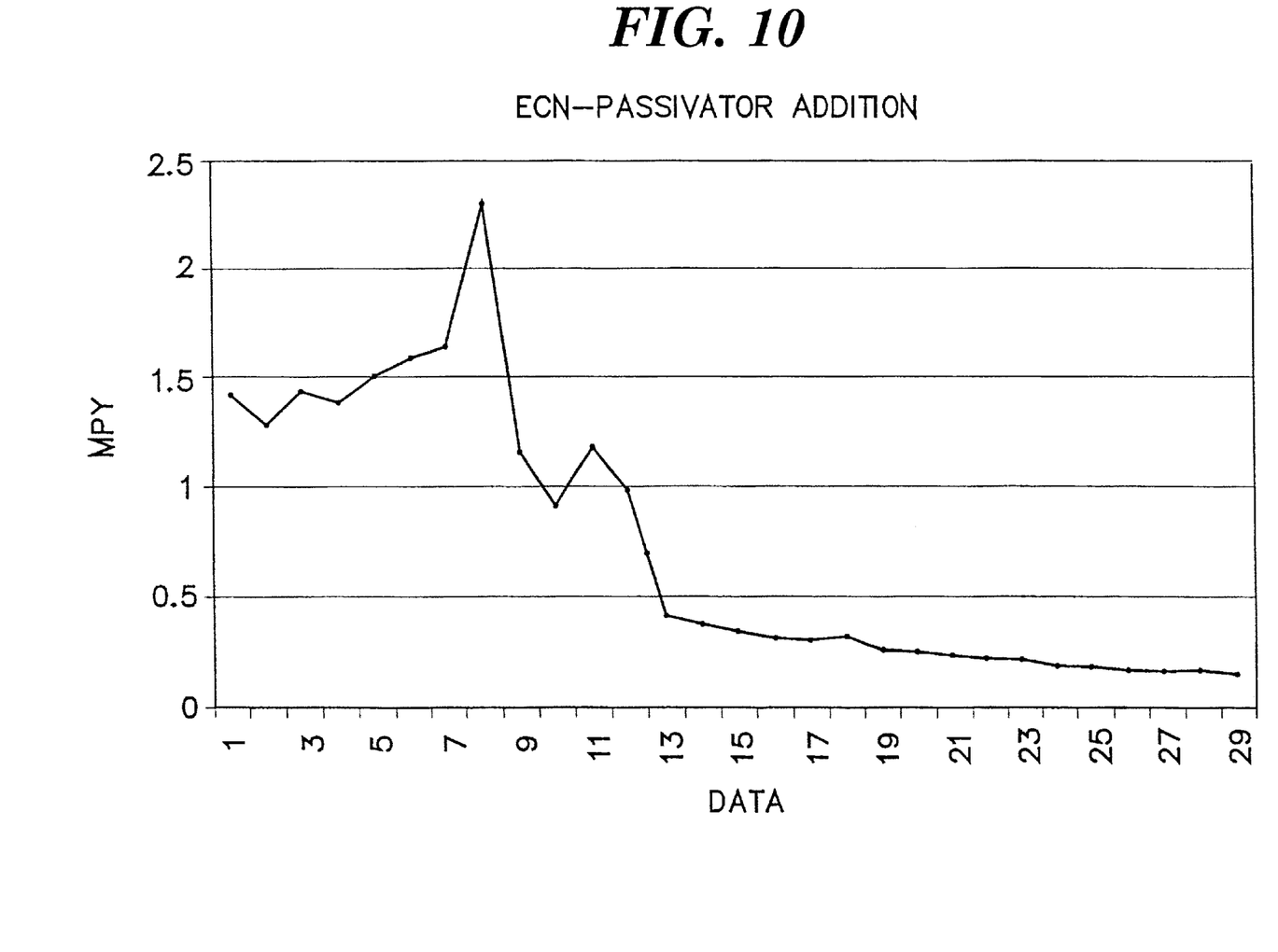
FIG. 10 is a graphical representation of Electrochemical Noise for a sample with passivator addition.

Test 3:

Referring now to FIGS. 9 and 10, the system was again tested under the same operating conditions except no passivating agent was added to the electrolyte (data points 1–6) The AF appeared steady state with fairly steady ECN corrosion rates. 50 ppm of passivating agent was added to the electrolyte.

The AF shows a magnitude increase. The LPR corrosion rate shows a significant decrease. The divergence indicates localized corrosion. This results from insufficient concentrations of passivator in the electrolyte. Distinct anodes exist thereby inducing localized corrosion.

An additional 50 ppm of passivator was added to the electrolyte. The AF again increases (data point 8 & 9) as does the LPR corrosion rate. This continuity in AF and LPR following the chemical addition indicates the current density is sufficient to induce rapid generalized corrosion across the electrodes surface (increase in the LPR corrosion values). Shortly thereafter, both LPR and ECN electrodes achieve a passive condition.

The system soon after (data point 12) approaches its steady state (passivated) condition.

Conclusions:

Monitoring the activity of the electrochemical noise current (AF) has been shown to be an effective tool in determining the steady state corrosion condition of the ECN electrode However, deviation from steady state does not necessarily indicate localized corrosion. AF, and other associated ECN values do not allow for the determination of the nature of corrosion without long-term power spectral analysis, during which time propagation of localized corrosion occurs.

It has now been discovered that when AF is correlated with LPR corrosion data, a powerful tool for consistent and reliable determination of the nature of corrosion results. This innovation has special application where corrosion inhibitors are used to inhibit corrosion of metal exposed to an electrolyte.

Results illustrate the ability to determine the nature of corrosion during the initial onset of corrosion by comparing, in real-time, the change in AF to the change in LPR corrosion rate (or associated LPR values). When AF detects a significant change in current activity as compared to the preceding steady state condition, an evaluation of the LPR corrosion rate is made and correlated with the AF value.

Divergence in the signals indicates localized corrosion. Continuity in signal pattern indicates generalized corrosion. Appropriate selection and addition of corrosion inhibitors and other supporting treatments can then be initiated in order to correct the condition and thwart the corrosive process.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A method for detecting onset of localized corrosion comprising:

measuring electrochemical noise (ECN);

measuring linear polarization corrosion rate (LPR);

calculating activity factor (AF) according to the equation:

$$AF = \sigma_i / i_{rms}$$

where $\sigma_i$ represents standard deviation of electrochemical noise current, and $i_{rms}$ is the root mean square of the electrochemical noise current; and performing a real-time evaluation of changes in AF values to changes in LPR corrosion rate values;

wherein divergence in said values is indicative of the onset of localized corrosion.

2. A method in accordance with claim 1 further including:

real-time selection and addition of corrosion inhibitors of a type and in an amount effective to prevent or suppress the propagation of said localized corrosion.

3. A process for detecting and forecasting the onset of localized corrosion at the metal-electrolyte interface of a heat exchanger comprising:

replicating the operational environment at the heat exchanger metal-electrolyte interface;

measuring electrochemical current noise (ECN);

measuring linear polarization corrosion rate (LPR);

calculating activity factor (AF) according to the equation:

$$AF = \sigma_i i_{rms}$$

where $\sigma_i$ represents standard deviation of electrochemical noise current, and $i_{rms}$ is the root mean square of the electrochemical noise current; and performing a real-time evaluation of changes in AF values to changes in LPR corrosion rate values;

wherein divergence in said values is indicative of the onset of localized corrosion within said heat exchanger.

4. A method in accordance with claim 3 further including:

real-time selection and addition of corrosion inhibitors of a type and in an amount effective to prevent or suppress the propagation of said localized corrosion.

* * * * *